(12) United States Patent
Paananen et al.

(10) Patent No.: US 7,001,521 B2
(45) Date of Patent: Feb. 21, 2006

(54) DISTRIBUTING OR COLLECTING DEVICE

(75) Inventors: Hannu Paananen, Kantvik (FI);
Heikki Heikkilä, Espoo (FI); Jari Lewandowski, Siuntio (FI); Esko Varteva, Kantvik (FI)

(73) Assignee: Finnfeeds Finland Oy, Espoo (FI)

( * ) Notice: Subject to any disclaimer, the term of this patent is extended or adjusted under 35 U.S.C. 154(b) by 40 days.

(21) Appl. No.: 10/373,504

(22) Filed: Feb. 25, 2003

(65) Prior Publication Data
US 2004/0129641 A1 Jul. 8, 2004

(30) Foreign Application Priority Data
Jan. 2, 2003 (FI) .................................. 20030007

(51) Int. Cl.
*B01D 15/08* (2006.01)
(52) U.S. Cl. .................. 210/656; 210/198.2; 210/289; 210/291; 210/456
(58) Field of Classification Search ................ 210/656, 210/198.2, 289, 291, 456; 95/82, 85; 96/101, 96/105, 107
See application file for complete search history.

(56) References Cited

U.S. PATENT DOCUMENTS

| 4,537,217 A | 8/1985 | Allen, Jr. ................. 137/561 A |
| 4,565,216 A | 1/1986 | Meier ...................... 137/561 R |
| 4,565,219 A | 1/1986 | Kunogi ................... 137/625.65 |
| 4,604,199 A | 8/1986 | Yoritomi ..................... 210/293 |
| 5,141,635 A | 8/1992 | LePlang et al. ........... 210/198.2 |
| 5,324,426 A | 6/1994 | Joseph et al. ............. 210/198.2 |
| 5,354,460 A | 10/1994 | Kearney et al. .......... 210/198.2 |
| 5,423,982 A | 6/1995 | Jungbauer et al. ....... 210/198.2 |
| 5,846,411 A | 12/1998 | Harter et al. ............. 210/198.2 |

FOREIGN PATENT DOCUMENTS

| WO | WO 00/50144 | 8/2000 | ............... 210/198.2 |
| WO | WO 02/05923 A1 | 1/2002 | ............... 210/198.2 |

OTHER PUBLICATIONS

Kochergin, et al., "Fractal Structures for Uniform Fluid Distribution in the Sugar Industry", *Zuckerindustrie 126*, (2001) Nr. 1, pp. 51 to 54.

*Primary Examiner*—Ernest G. Therkorn
(74) *Attorney, Agent, or Firm*—Sterne, Kessler, Goldstein & Fox P.L.L.C.

(57) ABSTRACT

The present invention relates to a fluid distributing device for distributing fluid into a column and to a fluid collecting device for collecting fluid from a column. The invention relates also to methods of using the devices of the present invention. The distributing device and/or the collecting device of the present invention can be used in fixed or fluidized bed reactors or columns, such as chromatographic separation columns, ion exchange columns, adsorption columns etc. A fluid distributing device comprises
a) a first fluid conveying system; and
b) a distributing plate, which comprises
i) first means for fluid transfer for dividing the fluid flow coming from the delivering points into several partial fluid flows and for distributing the partial fluid flows into the column; and
ii) first means for controlling of the partial fluid flows by differential pressure in the first means for fluid transfer.

13 Claims, 8 Drawing Sheets

DISTRIBUTING OR COLLECTING DEVICE

FIELD OF THE INVENTION

The present invention relates to a fluid distributing device for distributing fluid into a column. The present invention relates also to a fluid collecting device for collecting fluid from a column. The invention relates also to methods of using the devices of the present invention.

The distributing device and/or the collecting device of the present invention can be used in fixed or fluidized bed reactors or columns, such as chromatographic separation columns, ion exchange columns, adsorption columns etc.

BACKGROUND OF THE INVENTION

A common problem associated with the distributing devices is that the fluid to be distributed is introduced to a column through a pipe, which has a relatively small diameter compared to the diameter of the column. The fluid has to be distributed evenly over the entire cross-section area of the column and with minimum time delay and time delay distribution. Likewise a collecting device should collect fluid from a column evenly and with minimum time delay and time delay distribution and convey the fluid further to a pipe. This is especially important and hard to accomplish when the cross-section area of the column is large, and/or especially when the column length is short. Both the distributing and collecting devices should have a minimum mixing volume of the fluid fronts. This means that e.g. in a chromatographic column operation the concentration gradient between for example the feed and the eluent should stay distinctive, and this also enables the feeding of the separation profile into a subsequent column, if needed and when needed. To minimize the mixing volume the devices should be in close connection with the column filling material. At the same time the devices should prohibit the column filling material from clogging into the distributing or collecting device. When the distributing and/or collecting devices are situated completely outside the column filling material they enable geometrically ideal shape for the column filling material bed. The distributing and collecting devices should also have a low pressure drop.

In U.S. Pat. No. 4,537,217 is described a fluid separator apparatus and a method of fluid distribution adapted for chromatography applications. The fluid separator apparatus comprises distribution plates, which have recursive channels on one side of the plate and evenly distributed holes on the other side of the plate. The recursive channels have substantially uniform length and similar geometric flow resistance. Channels with recursive T-joints are also shown in the application. However, there are several disadvantages related to this realisation. One of the embodiments of the invention described in the US patent is applicable as such only in a column, which is square in cross-section. In the US patent is described also a solution for columns with circular cross-section. For circular columns the separator apparatus comprises distribution openings, which are located within areas defined by the perimeters of concentric circles. However, the application for columns with circular cross-section is very difficult to scale up to be used in columns with substantially larger diameter than 0,3 m.

In U.S. Pat. No. 4,604,199 is described a filtration column which has a bottom with reciprocally arranged peaks and troughs. In the troughs lie branched pipes with uniformly distributed small holes on their lower portions and which are surrounded by screens or wedge pipes. The branched pipes lead to gathering pipes, which in turn lead to an outlet. This kind of arrangement is prone to mechanical and constructional problems caused by the expanding and contracting of the column filling material. One problem associated with this kind of arrangement is that the device causes heavy mixing in the flowing fluid fronts and this means that the separation medium is not able to work efficiently. Heavy mixing in the fluid fronts is caused because the device is arranged within the column filling material.

In U.S. Pat. No. 5,423,982 is described a liquid chromatography column adapted for in situ chemical sterilisation. The column includes a distributor for distributing fluid conducted through the fluid distribution channel over the entity of the orifice. The distributor is preferably a metal plate, either in the form of a multilayer sintered metal filter, a perforated plate with a hole diameter less than the lower grain diameter of the resin particles, or a woven and/or sintered stainless steel monolayer welded onto a metal ring.

In U.S. Pat. No. 5,324,426 is described a chromatographic column in which one or more of the end plates defining the column are provided with specially designed lands and grooves to distribute the input liquid over the column cross-section area. The distribution plates comprise radially oriented fluid passages of decreasing depth going from the centre of the plate to the circumference.

In U.S. Pat. No. 5,141,635 is described a fluid distributor, which comprises a separator consisting of a disc of porous material, and a distribution plate which comprises on its face annular channels connected to a feed/discharge line by conduits. These channels are joined by a hole through the plate, which has a pressure drop. The pressure drop is inversely proportional to the area of the channels. The US patent also describes the use of porous plates between the resin bed and the distribution plates preventing the resin from entering the channels.

In U.S. Pat. No. 5,354,460 is described fluid transfer system with uniform fluid distributor. In the distributor step-down nozzles with recursive flow channels are used. The step-down nozzles are arranged side by side in concentric rings around a center well.

In U.S. Pat. No. 4,565,216 is described a device for gravimetric distribution of liquid for mass and heat transfer columns. The device employs a container with pipe outlets, a plurality of individual distributors in the form of manifolds and metering devices between the container and individual distributors for metering the partial flows of liquid to the individual distributors. In the US patent is shown that the cross-section of the column is divided into 6 sectors and a hexagonal centre part.

Kochergin and Kearney (Zuckerindustrie 126 (2001) no. 1, 51–54) describe fractal structures for fluid distribution. Fractal means in this connection recursive generations of divisions of flow into channels, which are substantially similar. Achieving the needed degree of performance means that a large number of generations must be used in the engineered fractals and this makes the systems very complicated and expensive.

Problems related to the above described prior art solutions are poor liquid distribution to the whole cross-section area of the column or poor liquid collection from the whole cross-section area of the column or complicated and expensive construction of the distributing and/or collecting device, especially when large columns are used. Poor distribution or collection of the fluid e.g. in a chromatographic column operation results in mixed fluid fronts, increased time delay and time delay distribution. Fluid front means the concentration gradient between different components in the moving phase, for example the concentration gradient between the feed and the eluent. Time delay in the distributing and/or collecting device is the volume of the device divided by the flow rate of the fluid. Time delay distribution is the spread of the distributing/collecting times. Minimum time delay distribution means that the fluid introduced to a column is distributed from each point in the distributing device essentially at the same time or that the fluid flowing out of a column is collected from each point in the collecting device essentially at the same time. Many of the prior art solutions result in large mixing volumes of the fluid fronts. The mixing of the fluid fronts results in dilution in the column. This results further in that the efficiency of the column filling material is poorer and this means that the separation of the desired components is inadequate or requires a larger volume of the column filling material. The operating costs increase when dilution takes place in the column.

BRIEF DESCRIPTION OF THE INVENTION

An object of the present invention is thus to provide a device and a method to alleviate the above disadvantages. The objects of the invention are achieved by devices, which are characterized by what is stated in the independent claims. The preferred embodiments of the invention are disclosed in the dependent claims.

The invention is based on the idea of distributing to and collecting from a column, for example a chromatographic column, a fluid with minimum time delay, minimum time delay distribution and minimum mixing volume of the fluid fronts.

The fluid distributing device of the present invention comprises a) a first fluid conveying system, through which the fluid flow is delivered to delivering points; and b) a distributing plate, which comprises i) first means for fluid transfer, which are adapted to divide the fluid flow coming from the delivering/distributing points into several partial fluid flows and to distribute the partial fluid flows further through the cross-section area of a column; and ii) first means for controlling of the partial fluid flows to the partial sections by differential pressure in the first means for fluid transfer.

The fluid collecting device of the present invention comprises a) a collecting plate, which comprises i) second means for fluid transfer, which are adapted to collect from a column several partial fluid flows and to convey the fluid flows to the collecting/receiving points; and ii) second means for controlling the pressure of the partial fluid flows by differential pressure in the second means for fluid transfer; and b) a second fluid conveying system for delivering/collecting the fluid flow from the collecting/receiving points.

The distributing device of the present invention solves the problem of distributing fluid into a column evenly with minimum time delay, with minimum time delay distribution and with minimum mixing of the fluid fronts.

The distributing device of the present invention comprises means for fluid transfer, especially distributing channels from which the fluid can be distributed to a column. The fluid can be distributed to a column evenly from the entire length of the distributing channel or from part of the distributing channel. This is achieved by the means for controlling the fluid flows to the partial sections in the plate. The means for controlling the fluid flows provide differential pressure, which causes the fluid flow to be distributed evenly.

The means for controlling the fluid flow can be nozzles or openings. The nozzles or openings can be situated between a fluid transfer port and a distributing channel, between a fluid transfer port and a connecting channel or between a connecting channel and a distributing channel.

The means for controlling the fluid flow can alternatively be a disk with apertures. The disk with apertures can be situated after the distributing channels.

The even distribution of the fluid is also achieved by constructing the means for fluid transfer so that the cross-section area of the means for fluid transfer diminishes as the amount of fluid flow diminishes in the means for fluid transfer.

The collecting device of the present invention solves the problem of collecting fluid from a column evenly with minimum time delay, with minimum time delay distribution and with minimum mixing of the fluid fronts.

The collecting device of the present invention comprises means for fluid transfer, especially collecting channels to which the fluid is collected from a column. The fluid can be collected from a column evenly from the entire length of the collecting channel or from a part of the collecting channel. This can be achieved by the means for controlling the fluid flows from the partial sections in the plate. The means for controlling the fluid flow provide differential pressure, which causes the fluid flow to be collected evenly.

The means for controlling the fluid flow can be nozzles or openings. The nozzles or openings can be situated between fluid transfer port and a collecting channel, between fluid transfer port and a connecting channel or between a connecting channel and a collecting channel.

The means for controlling the fluid flow can alternatively be a disk with apertures. The disk with apertures can be situated before the collecting channels. The even collection of the fluid is also achieved by constructing the means for fluid transfer so that the cross-section area of the means for fluid transfer increases as the amount of fluid flow increases in the means for fluid transfer.

An advantage of the present invention is that the fluid is distributed and collected evenly across the whole cross-section area of the column, for example a chromatographic column, with minimum time delay, minimum time delay distribution and minimum mixing of the fluid fronts. The fluid is also distributed and/or collected with minimum turbulence throughout the cross-section of the column. The lack of time delay and minimum time delay distribution in the distributing and/or collecting of the fluid in a separation operation enhances the separation of the desired fractions. Another advantage of the present invention is that when the distributing and/or collecting device of the present invention is used in a column, for example a chromatographic column, the mixing volumes of the fluid fronts are at minimum. The small mixing volume of the fluid front enables a better utilisation of the column filling material. This means that a better separation of the desired products can be achieved with a smaller amount of column filling material. All this results further in lower investment costs.

Yet another advantage of the present invention is that the column filling material is kept apart from the distributing and/or collecting device and the column filling material does not clog the distributing and/or collecting devices. Another advantage of the distributing device and/or collecting device of the present invention is that they can advantageously be operated with low pressure drop. One of the advantages of the present invention is also that the use of the distributing and/or collecting device causes less dilution and the operating of a plant using either one or both of these devices is improved. This results also in small energy consumption e.g. because of lower concentrations are demanded. The devices of the present invention are also easily cleaned and it is possible to assemble and disassemble them easily to and from the column. One of the advantages of the present invention is also that they are especially useful in columns, which have a large cross-section area and a short bed length.

BRIEF DESCRIPTION OF THE DRAWINGS

In the following the invention will be described in greater detail by means of preferred embodiments with reference to the attached drawings, in which

FIG. 2 shows a distributing device from above, which comprises first fluid conveying system 1, delivering points 2 and a column top plate 3a;

DETAILED DESCRIPTION OF PREFERRED EMBODIMENTS OF THE INVENTION

Figure 1:
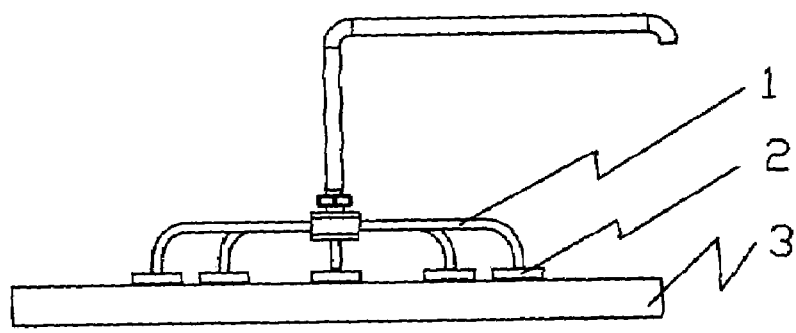
FIG. 1 shows a distributing device from the side, which comprises first fluid conveying system 1, delivering points 2 and a distributing plate 3.

The fluid distributing device of the present invention comprises a) a first fluid conveying system 1, through which the fluid is delivered to the delivering points 2; and b) a distributing plate 3, which comprises i) first means for fluid transfer 4; 5; 5a; 5b, which are adapted to divide the fluid flow coming from the delivering points 2 into several partial flows and distributing the partial flows further; and ii) first means 6 for controlling the partial fluid flows to the first partial sections by differential pressure.

Figure 2:
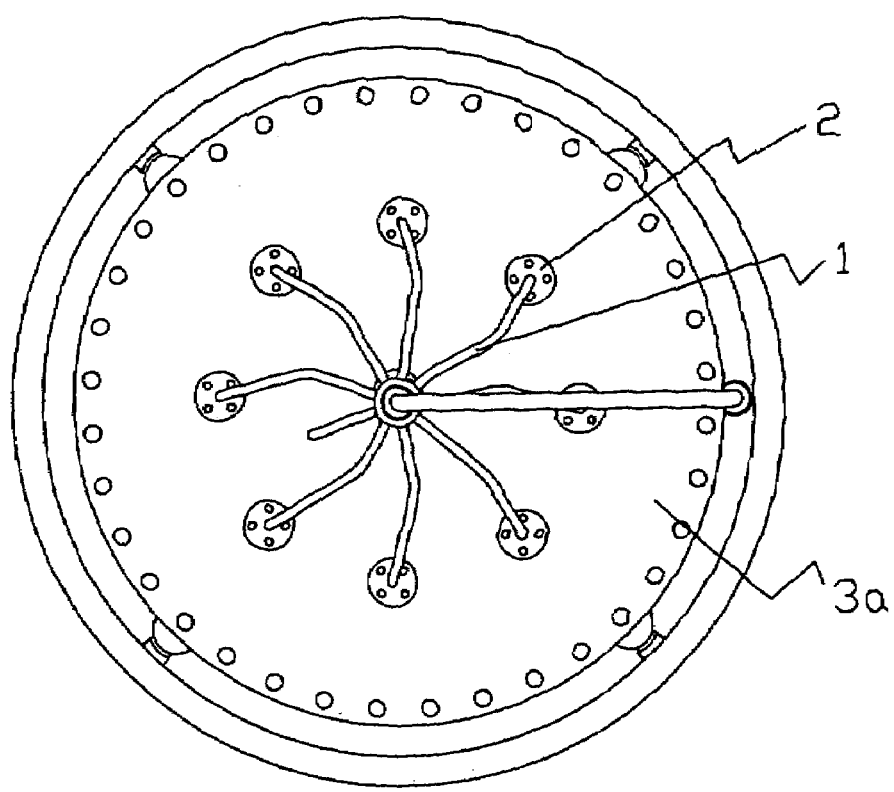
Figure 3:
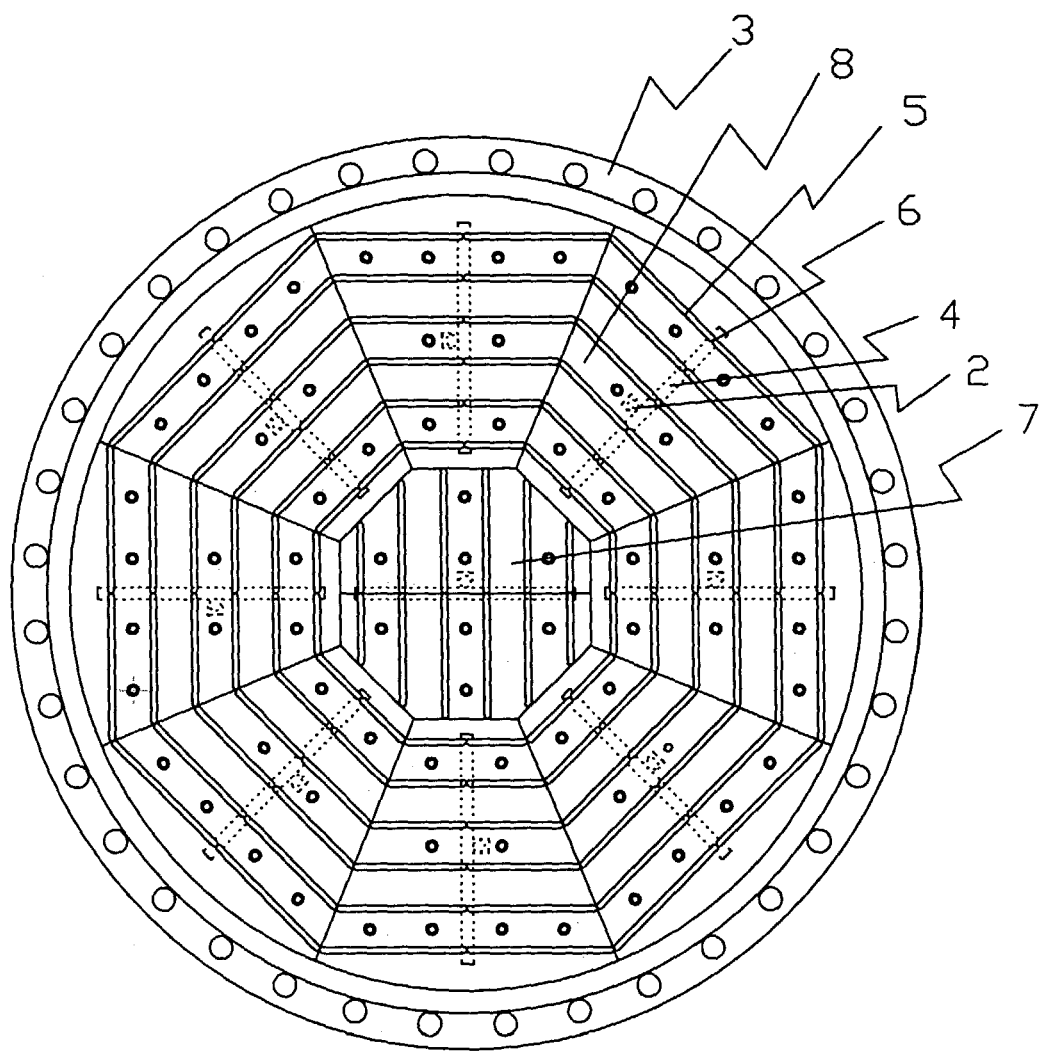
FIG. 3 shows the distributing plate 3, which comprises distributing points 2, a first centrepiece 7, a number of first sectors 8, first fluid transfer ports 4, distributing channels 5 and first means 6 for controlling the partial flows.
Figure 4:
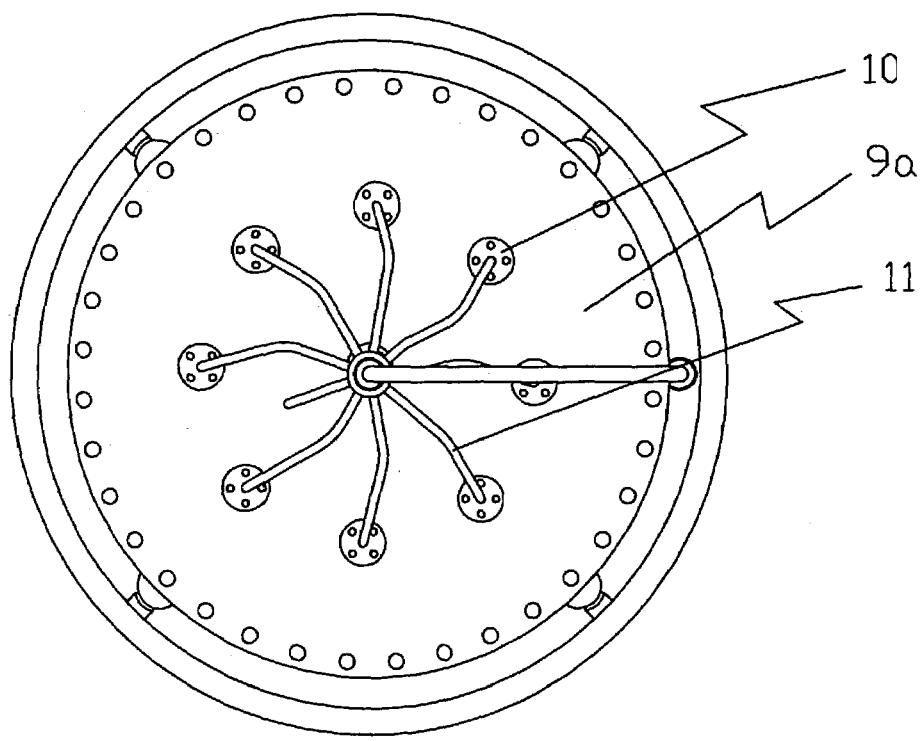
FIG. 4 shows a collecting device from below, which comprises column bottom plate 9a, collecting points 10 and a second fluid conveying system 11.
Figure 5:
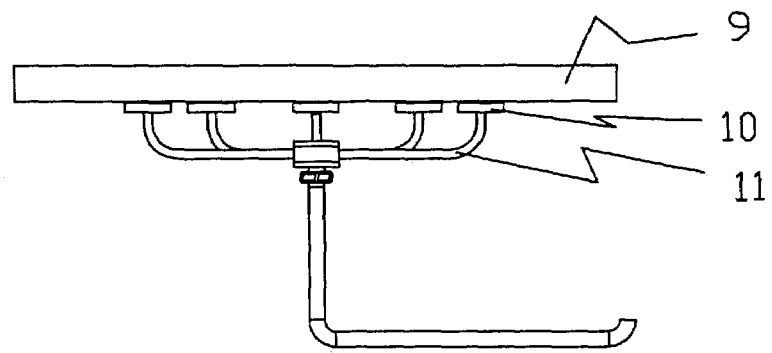
FIG. 5 shows a collecting device from the side, which comprises collecting plate 9, collecting points 10 and a second fluid conveying system 11.
Figure 6:
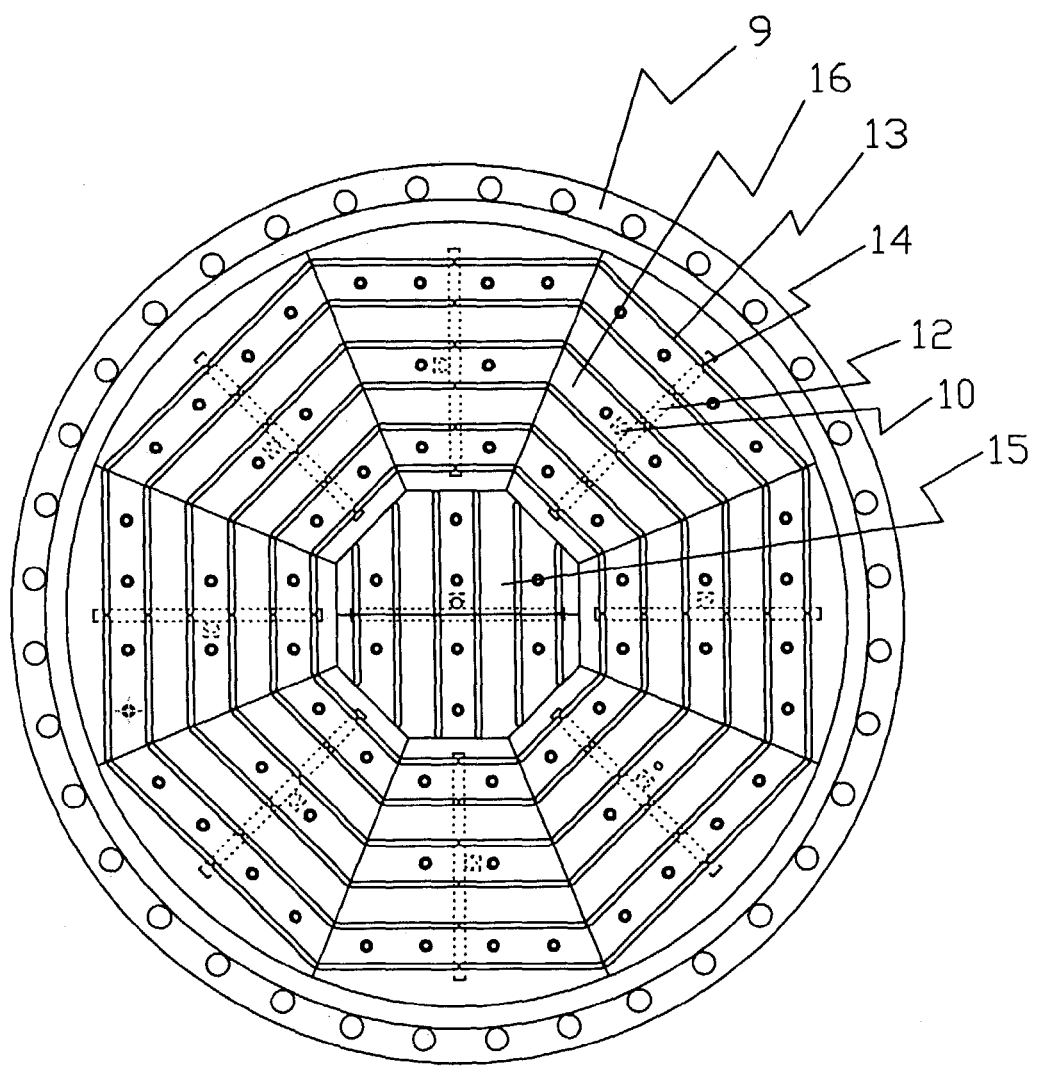
FIG. 6 shows the collecting plate 9, which comprises collecting points 10, a second centrepiece 15, a number of second sectors 16, second fluid transfer ports 12, collecting channels 13 and second means 14 for controlling the partial flows.

The first fluid conveying system 1 can be constructed by using a number of pipes as shown in FIG. 2. It can also be constructed by using a master plate. The master plate comprises channels for conveying fluid or the master plate may be constructed by using pipes embedded in the plate. The master plate can advantageously be situated inside the column between the column top plate 3a and the distributing plate 3.

The first means for fluid transfer can be for example first fluid transfer ports 4 or first channels 5; 5a; 5b. The first fluid transfer ports can be for example channels, or they can have a circular or prolate shape. The channels can be connecting channels 5a or distributing channels 5; 5b.

In one embodiment of the present invention the distributing plate comprises first fluid transfer ports 4 and distributing channels 5. In another embodiment of the present invention the distributing plate comprises first fluid transfer ports 4 and first connecting channels 5a connecting the first fluid transfer ports 4 with the distributing channels 5b. The shape of the first fluid transfer port may vary, and it can be for example circular or prolate.

The distributing plate 3 is divided into several first sections, which comprise a first centrepiece 7 and a number of first sectors 8. The first centrepiece 7 has generally a shape of a polygon, preferably it has a shape of a regular polygon. The first centrepiece can have for example a shape of a square, pentagon, hexagon or an octagon or of a polygon of higher order. The first centrepiece can also have a circular shape. Preferably the first centrepiece has a shape of an octagon. The distributing plate may also be constructed without a first centrepiece. The first sectors 8 can be in one or more rings around the first centrepiece 7. Usually the first sectors form one ring around the first centrepiece, but if the diameter of the column is relatively large (for example larger than 1 m) the first sectors may be in two or more rings around the first centrepiece. The number of first sectors 8 in the ring next to the first centrepiece 7 corresponds advantageously to the number of the sides of the first centrepiece. For example if the first centrepiece has a shape of an octagon the number of first sectors in the ring next to the first centrepiece is 8. The number of first sectors in the outer ring is for example two times the number of first sectors in the inner ring next to it. This means that if the first centrepiece has a shape of an octagon the number of first sectors in the ring next to the first centrepiece is 8 and the number of first sectors in the ring next to the first ring is from 14 to 16. Advantageously the area of the first centrepiece is approximately equal to the area of each first sector, or advantageously the area of the first centrepiece is approximately twice the area of the first sector.

A support plate can be used in the distributing device of the present invention. The sectors or the distributing plate may be attached to the support plate.

In one embodiment of the present invention the first means for fluid transfer on the distributing plate 3 comprises first fluid transfer ports 4 from which the fluid flows through first means 6 for controlling the partial flows to distributing channels 5. The first means 6 for controlling the partial flows are dimensioned so that the amount of fluid passing through the first means is in ratio to the distributing area served by the corresponding distributing channel. The first fluid transfer ports 4 can be perpendicular to the distributing channels and preferably the delivering point 2 is approximately in the middle of the first fluid transfer port 4. Advantageously the pressure drop of the first means for controlling the partial flows is significant compared to the pressure drop taking place in other parts of the distributing plate.

The first fluid transfer ports 4 and the distributing channels 5 can be on the same side of the distributing plate, but generally the distributing plate 3 comprises first fluid transfer ports 4 on the outer side of the distributing plate and distributing channels 5 on the inner side of the distributing plate. Outer side of the distributing plate means in this context the side of the distributing plate facing outwards of the column filling material, for example chromatographic resin, in the column. Inner side of the distributing plate means in this context the side of the distributing plate facing inwards of the column filling material in the column. The first fluid transfer ports and the distributing channels can be also constructed using pipes.

In another embodiment of the present invention the first means for fluid transfer on the distributing plate 3 comprise first fluid transfer ports 4 from which the fluid flows through the first means 6 for controlling the partial flows to the first connecting channels 5a. The first connecting channels 5a connect the first fluid transfer ports 4 and the distributing channels 5b. From the distributing channels 5b the fluid is distributed over the cross-section area of the column. The first connecting channels 5a and the distributing channels 5b can also be constructed using pipes. The first means 6 for controlling the partial flows can also be situated between the first connecting channels 5a and the distributing channels 5b. The first means 6 for controlling the partial flows are dimensioned so that the amount of fluid passing through the first means for controlling the partial flows is in ratio to the distributing area served by the corresponding distributing channel.

The first fluid transfer ports 4 and/or the connecting 5a and distributing channels 5b can be on the same side of the distributing plate, but generally the distributing plate 3 comprises first fluid transfer ports 4 and the connecting channels 5a on the outer side of the distributing plate and distributing channels 5b on the inner side of the distributing plate. Outer side of the distributing plate means in this context the side of the distributing plate facing outwards of the column filling material, for example the chromatographic resin bed in the column. Inner side of the distributing plate means in this context the side facing the column filling material in the column. The first fluid transfer ports 4 and the distributing channels 5b can also be constructed using pipes.

The first means 6 for controlling the partial flows comprise nozzles and/or openings. The distributing plate may also be constructed without nozzles but with openings using e.g. a disk with apertures.

The distances between the channels are preferably constant. The distributing plate comprises distributing channels in such a manner that the length of the distributing channels per unit of area is advantageously essentially constant throughout the distributing plate.

The distributing channels are constructed in a way, which gives even distribution of the fluid throughout the cross-section area of the column. The distributing channels are dimensioned in a manner, which ensures that the linear flow rate stays even and essentially constant, for example for water-sugar-solution this means that the linear flow rate is between 0,2–4 m/s, in the channels. In order to keep the linear flow constant in the first fluid transfer ports the cross-section area of the first fluid transfer port 4 preferably diminishes gradually from the delivering point 2 towards the end of the first fluid transfer port. In order to keep the linear flow constant in the distributing channels the cross-section area of the distributing channel 5 diminishes gradually from the first means 6 for controlling the partial flow, e.g. from a nozzle or an opening, towards the end of the distributing channel. The size of the distributing channels 5 is designed so that an even amount of fluid per unit area is distributed along the distributing channels to the column filling material. The volumetric flow rate of the fluid through the channels decreases due to the fluid leaving the channel. This design of the channels minimizes the time delay, time delay distribution and mixing volume of the fluid fronts distributed to the column. Preferably the relation of the sum of the lengths of the channels to a unit of area is essentially constant across the distributing plate.

A distributing plate can be prepared of a suitable metal or plastics, such as for example stainless steel or polysulfone. The plate comprises channels that are for example routed, etched, sawed or molded into the plate surface.

A first means for keeping the column filling material apart from the distributing plate can be used in the distributing device. The means can be for example a screen or net and it can be situated between the distributing plate and the column filling material. The screen or net prevents the column filling material of moving through it to the distributing channels of the distributing plate and blocking the distributing channels. The screen or net can be a combination of stainless steel meshes or a metal sintered plate or a combination thereof like Dynapore® and Fujiplate®, or it can be a screen made of conical wire sold by Johnson Screens or by Euroslot S.A. One object of the net or screen placed before the column filling material is to eliminate extra kinetic energy. The distribution of the fluid can be enhanced by placing an extra net or screen in the column after the distributing channels.

The present invention relates also to a method for distributing fluid in a column, in which method the above described fluid distributing device is used and the method comprises the steps of a) feeding the fluid to the first fluid conveying system 1;

b) delivering the fluid to the delivering points 2;

c) distributing the fluid from the delivering points 2 into the first fluid transfer ports 4;

d) distributing the fluid from the first fluid transfer ports 4 into the distributing channels 5; 5b optionally through the first means 6 for controlling the partial flows and through the first connecting channels 5a; and e) distributing the fluid from the distributing channels 5; 5b evenly throughout the cross-section of the column.

The present invention relates to a collecting device. The collecting device of the present invention can be constructed in the same way as the distributing device described above, and it is placed in e.g. a chromatographic column so that the side of the collecting plate comprising the collecting channels is facing towards the filling material in the column.

The fluid collecting device of the present invention comprises a) a collecting plate 9 comprising i) second means for fluid transfer 13; 13a; 13b; 12, which are adapted to collect the fluid flow form several partial flows and conveying the flows to the collecting points 10; and ii) second means 14 for controlling the partial fluid flows to the second partial sections by differential pressure; and b) a second fluid conveying system 11 to which the fluid is collected through the collecting points 10.

The collecting plate 9 is divided into several second sections, which comprise a second centrepiece 15 and a number of second sectors 16. The second centrepiece 15 has generally a shape of a polygon, preferably it has a shape of a regular polygon. The second centrepiece can have for example a shape of a square, pentagon, hexagon or an octagon or of a polygon of higher order. The second centrepiece can also have a circular shape. Preferably the second centrepiece has a shape of an octagon. The collecting device may also be constructed without a second centrepiece. The second sectors 16 can be in one or more rings around the second centrepiece. Usually the second sectors form one ring around the second centrepiece, but if the diameter of the column is relatively large (for example larger than 1 m) the second sectors may be in two or more rings around the second centrepiece. The number of second sectors 16 in the ring next to the second centrepiece 15 corresponds advantageously to the number of the sides of the second centrepiece. For example if the second centrepiece has a shape of an octagon the number of second sectors in the ring next to the second centrepiece is 8. The number of second sectors in the outer ring is for example two times the number of second sectors in the inner ring next to it. This means that if the second centrepiece has a shape of an octagon the number of second sectors in the ring next to the second centrepiece is 8 and the number of second sectors in the ring next to the first ring is from 14 to 16. Advantageously the area of the second centrepiece is equal to the area of each second sector, or advantageously the area of the centrepiece is twice the area of the second sector.

A support plate can be used in the collecting device of the present invention. The sectors or the collecting plate may be attached to the support plate.

The second means for fluid transfer can be for example second fluid transfer ports 12 or channels 13; 13*a*; 13*b*. The second fluid transfer ports can be for example channels, or they can have a circular or prolate shape. The channels can be connecting channels 13*a* or collecting channels 13; 13*b*.

In one embodiment of the present invention the collecting plate comprises second fluid transfer ports 12 and collecting channels 13. In another embodiment of the present invention the collecting plate comprises second fluid transfer ports 12 and second connecting channels 13*a* connecting the second fluid transfer ports 12 with the collecting channels 13*b*. The shape of the second fluid transfer port may vary, and it can be for example circular or prolate.

In one embodiment of the present invention the second means for fluid transfer on the collecting plate 9 comprise second fluid transfer ports 12 to which the fluid is collected through the second means for controlling the partial flows from the collecting channels 13. The second means for controlling the partial flows are dimensioned so that the amount of liquid passing through the second means is in ratio to the collecting area served by the corresponding collecting channel and they provide essentially equal pressure drops. The second fluid transfer ports 12 can be perpendicular to the collecting channels 13 and preferably the collecting point 10 is approximately in the middle of a second fluid transfer port 12. Advantageously the pressure drop of the second means for controlling the partial flows is significant compared to the pressure drop taking place in other parts of the collecting plate.

The second fluid transfer ports and the collecting channels can be on the same side of the collecting plate, but generally the collecting plate 9 comprises second fluid transfer ports 12 on the outer side of the collecting plate and collecting channels 13 on the inner side of the collecting plate. Outer side of the collecting plate means in this context the side of the collecting plate facing outwards of the column filling material, for example chromatographic resin, in the column. Inner side of the collecting plate means in this context the side of the collecting plate facing inwards of the column filling material in the column. The second fluid transfer ports and the collecting channels can be also constructed using pipes.

In another embodiment of the present invention the second means for fluid transfer on the collecting plate 9 comprise second fluid transfer ports 12 to which the fluid is collected through the second means 14 for controlling the partial flows from the second connecting channels 13*a*. The second connecting channels connect the second fluid transfer ports and the collecting channels 13*b*. The fluid is collected to the collecting channels from the cross-section area of the column. The second connecting channels and the collecting channels can also be constructed using pipes. The second means for controlling the partial flows can also be situated between the second connecting channels and the collecting channels. The second means for controlling the partial flows are dimensioned so that the amount of fluid passing through the second means for controlling the partial flows is in direct ratio to the collecting area served by the corresponding collecting channel.

The second fluid transfer ports and/or the connecting and collecting channels can be on the same side of the collecting plate, but generally the collecting plate 9 comprises second fluid transfer ports 12 and the connecting channels 13*b* on the outer side of the collecting plate and collecting channels 13 on the inner side of the collecting plate. Outer side of the collecting plate means in this context the side facing outwards of the column filling material, for example the chromatographic resin bed in the column. Inner side of the collecting plate means in this context the side facing the column filling material in the column. The second fluid transfer ports and the collecting channels can be also constructed using pipes.

The second means 14 for controlling the partial flows comprise nozzles and/or openings. The distributing plate may also be constructed without nozzles but with openings using e.g. a disk with apertures.

The distances between the channels are preferably constant. The collecting plate comprises collecting channels in such a manner that the length of the collecting channels per unit of area is advantageously constant through out the collecting plate.

The collecting channels are constructed in a way, which gives even collection of the fluid through out the cross-section area of the column. The collecting channels are dimensioned in a manner, which ensures that the linear flow rate stays even and essentially constant, for example for a water-sugar-solution this means that the linear flow rate is between 0,2–4 m/s, in the channels. In order to keep the linear flow constant in the second fluid transfer ports the cross-section area of the second fluid transfer port 12 preferably diminishes gradually from the collecting point 10 towards the end of the second fluid transfer port. In order to keep the flow constant in the collecting channels the cross-section area of the collecting channel 13 increases gradually towards the second fluid transfer ports. The size of the collecting channels 13 is designed so that an even amount of fluid is collected along the collecting channels from the column. The volumetric flow rate of the fluid through the channels increases towards the second fluid transfer ports due to the fluid entering the channel. This design of the channels minimizes the time delay, time delay distribution and mixing volume of the fluid fronts in the column. Preferably the relation of the sum of the lengths of the channels to a unit of area is constant across the collecting plate.

A collecting plate can be prepared of a suitable metal or plastics, such as for example stainless steel or polysulfone. The plate comprises channels that are for example routed, etched, sawed or molded into the plate surface.

The second fluid conveying system 11 can be constructed by using a number of pipes. It can also be constructed by using a master plate. The master plate comprises channels for fluid conveying or the master plate may be constructed by using pipes embedded in the plate. The master plate can advantageously be situated inside the column between the column bottom plate 9a and the collecting plate 9.

A means for keeping the column filling material apart from the collecting plate can be used in the collecting device. The means can be for example a screen or net and it can be situated between the collecting plate and the column filling material. The screen or net prevents the column filling material of moving through it to the channels of the collecting plate and blocking the collecting channels. The screen or net can be a combination of stainless steel meshes or a metal sintered plate or a combination thereof like Dynapore® and Fujiplate®, or it can be a screen made of conical wire sold by Johnson Screens or by Euroslot S.A. The collection of the fluid can be enhanced by placing an extra net or screen to the column before the collecting channels.

The present invention also relates to a method for collecting fluid from a column, in which method the above described fluid collecting device is used and the method comprises the steps of a) collecting the fluid evenly from the cross-section of the column to the collecting channels 13; 13b;

b) conveying the fluid from the collecting channels 13; 13b to the second fluid transfer ports 12 through the second means 14 for controlling the partial flows;

c) conveying the fluid from the second fluid transfer ports 12 into the collecting points 10; and d) conveying the fluid from the collecting points 10 into the second fluid conveying system 11.

The present invention also relates to a separation system, for example a chromatographic separation system, which comprises the above described fluid distributing device and the above described fluid collecting device.

The present invention relates also to a method for separation, for example chromatographic separation, which method comprises i) a distributing phase in which the above described fluid distributing device is used and the distributing phase comprises the steps of a) feeding the fluid to the first fluid conveying system 1;

b) delivering the fluid to the delivering points 2;

c) distributing the fluid from the delivering points 2 into the first means for fluid transfer 4 d) distributing the fluid from the first means for fluid transfer 4 into the distributing channels 5; 5b through the first means 6 for controlling the partial flows and optionally through the first connecting channels 5a; and e) distributing the fluid from the distributing channels 5; 5b evenly throughout the cross-section of the column; and ii) a collecting phase in which an above described fluid collecting device is used and the collecting phase comprises the steps of f) collecting the fluid evenly from the cross-section of the column to the collecting channels 13; 13b g) conveying the fluid from the collecting channels 13; 13b to the second means for fluid transfer 12 through the second means 14 for controlling the partial flows and optionally through the second connecting channels 13a;

h) conveying the fluid from the second means for fluid transfer 12 into the collecting points 10; and j) conveying the fluid from the collecting points 10 into the second fluid conveying system 11.

The present invention relates also to a method of transferring a concentration gradient or part of a concentration gradient from one column to a subsequent column. The method comprises the steps of collecting the concentration gradient with the collecting device of the present invention from the bottom of a column and transferring the concentration gradient, for example through a pipe, to a subsequent column.

The present invention relates also to a method of collecting a concentration gradient from one column with the collecting device of the present invention and distributing the concentration gradient to a subsequent column with the distributing device of the present invention. The method comprises the steps of collecting the concentration gradient with the collecting device of the present invention from the bottom of a column and transferring the concentration gradient, for example through a pipe, and distributing the concentration gradient to the subsequent column with the distributing device of the present invention.

EXAMPLES

Example 1

Chromatography Test

Figure 7:
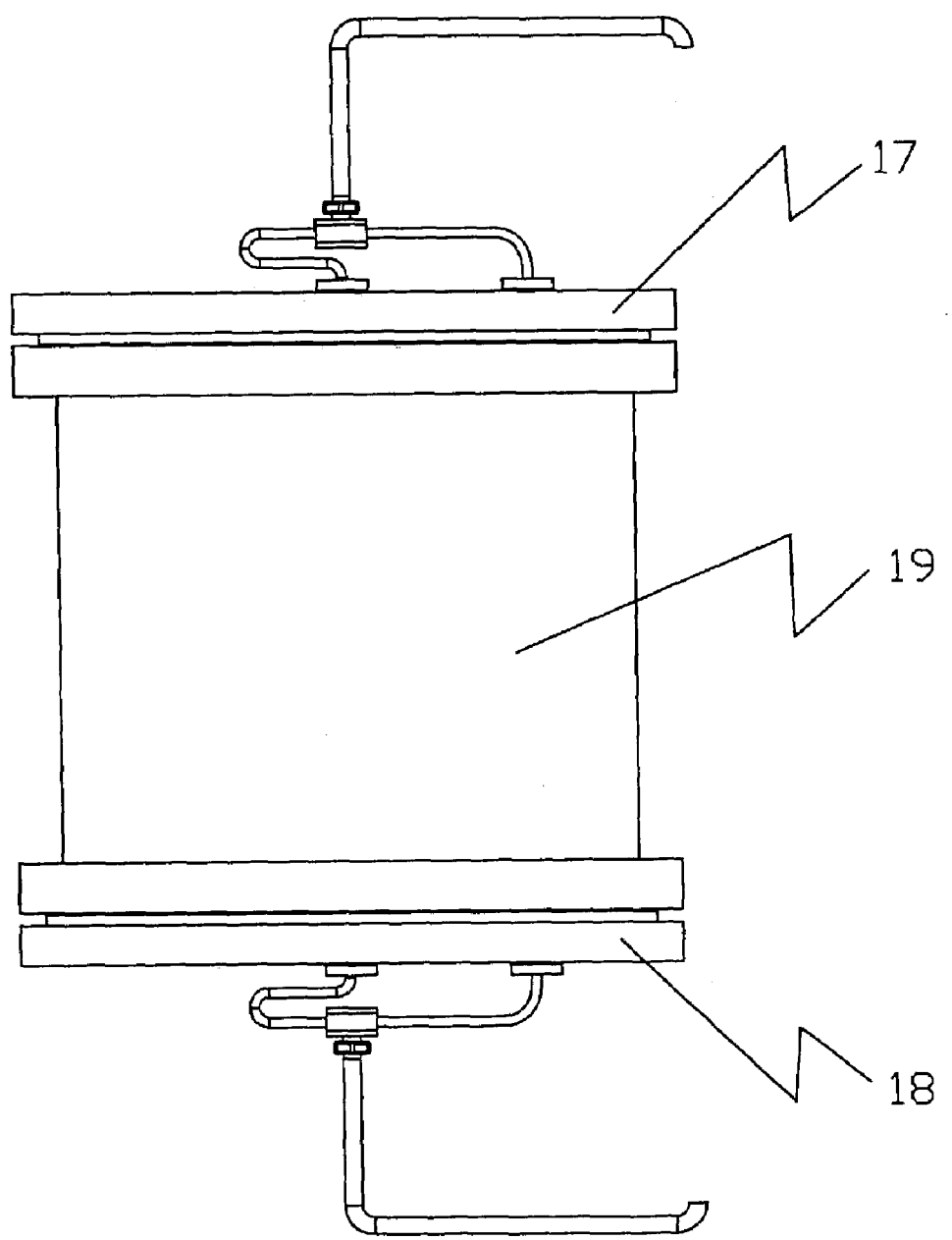
FIG. 7 shows a separation system, which comprises a distributing device 17, a separation column 19 and a collecting device 18.
Figure 8:
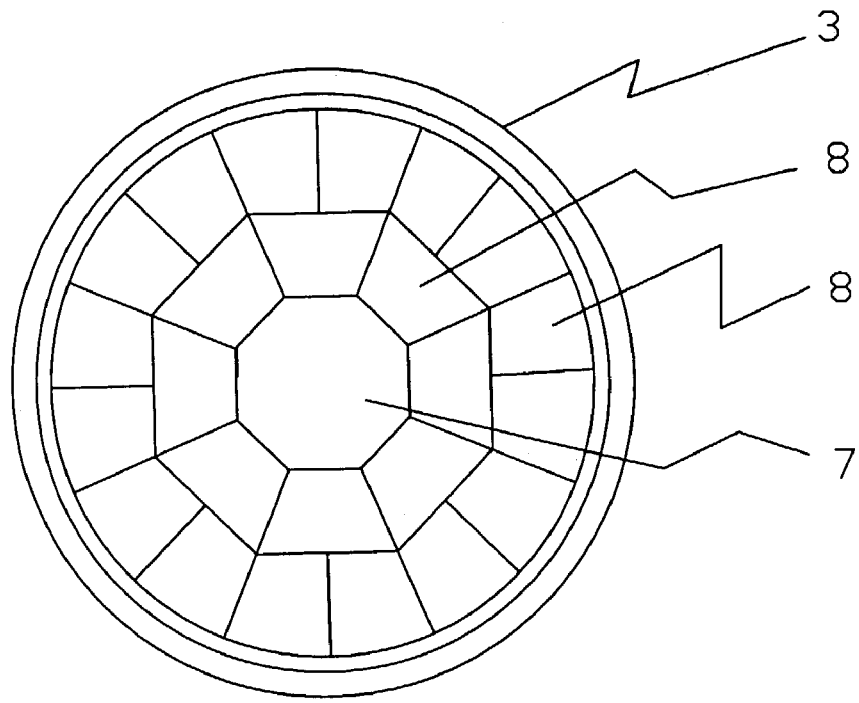
FIG. 8 shows a distributing plate 3, which comprises a first centrepiece 7 and a number of first sectors 8 and in which the number of first sections 8 is divided into two rings.
Figure 9:
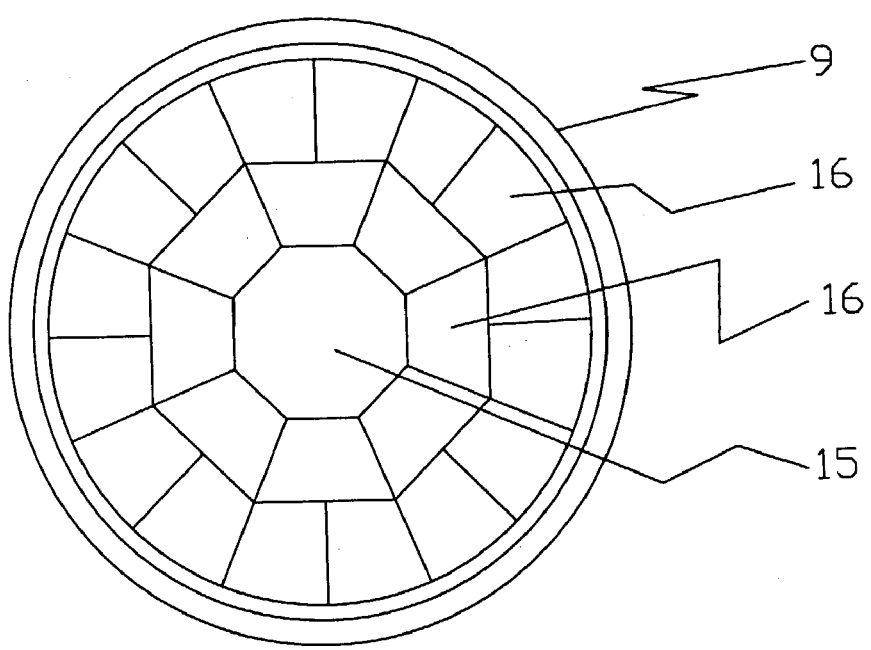
FIG. 9 shows a collecting plate 9, which comprises a second centrepiece 15 and a number of second sectors 16 and in which the number of second sectors 16 is divided into two rings.
Figure 10:
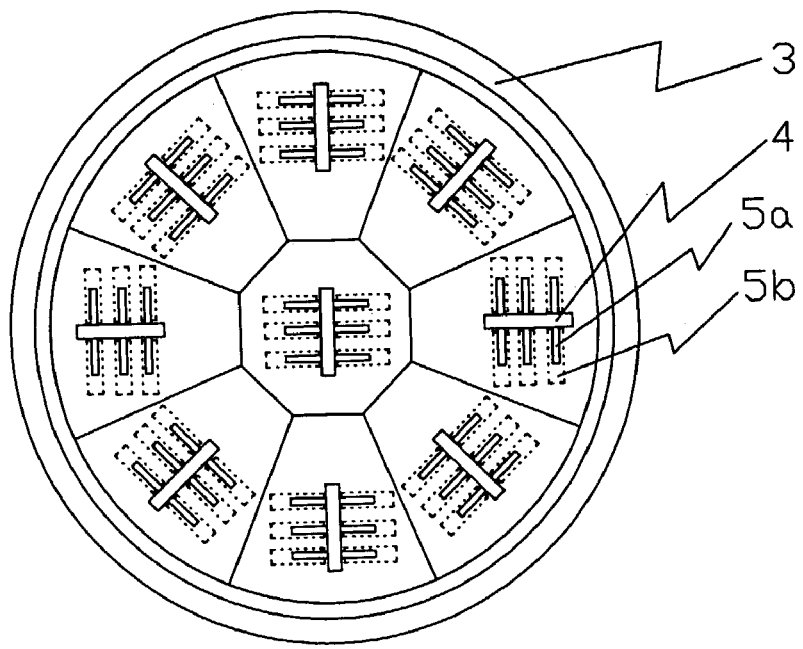
FIG. 10 shows a distributing plate 3, which comprises first fluid transfer ports 4, first connecting channels 5a and distributing channels 5b.
Figure 11:
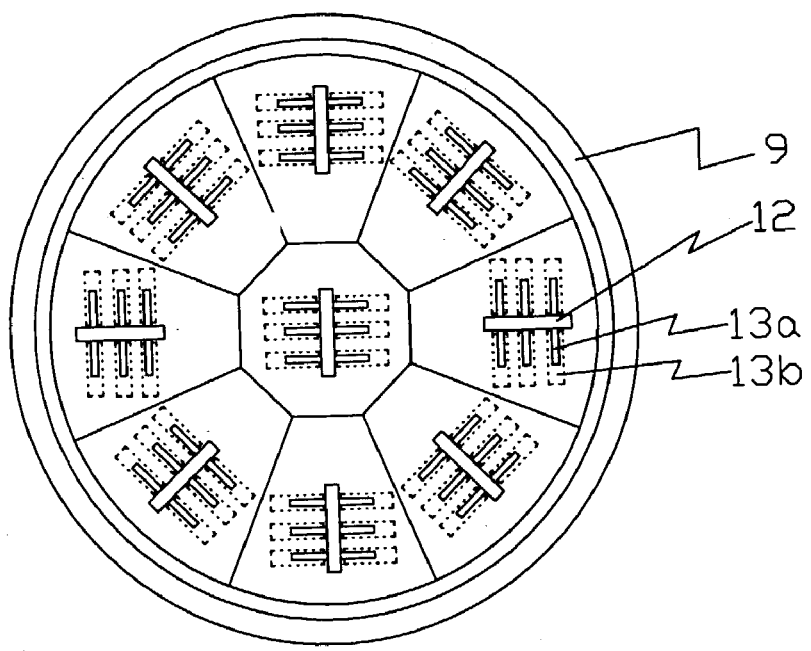
FIG. 11 shows a collecting plate 9, which comprises second fluid transfer ports 12, second connecting channels 13a and collecting channels 13b.

The test equipment included a column (such as for example in FIG. 7), a feed tank and an eluent tank, a feed solution pump and an eluent water pump and inlet valves for the both feed streams. The equipment included also a density meter (Micro Motion) to measure flow and density of the out coming flow and a flow control unit to control feed and eluent flows to the column. Pressure gauges were also placed in the column to measure liquid pressures at selected points: inlet liquid pressure (P1) and liquid pressure of resin bed after feed device (P2). Liquid pressure gauge P2 was isolated from the resin bed with a screen net.

The height of the column filling material bed was 1,0 m and diameter of the column filling material bed was 1,0 m. The column was packed with a strong acid gel type cation exchange resin (MitsubishiUBK 530) in $Na^+$-form.

Figure 12:
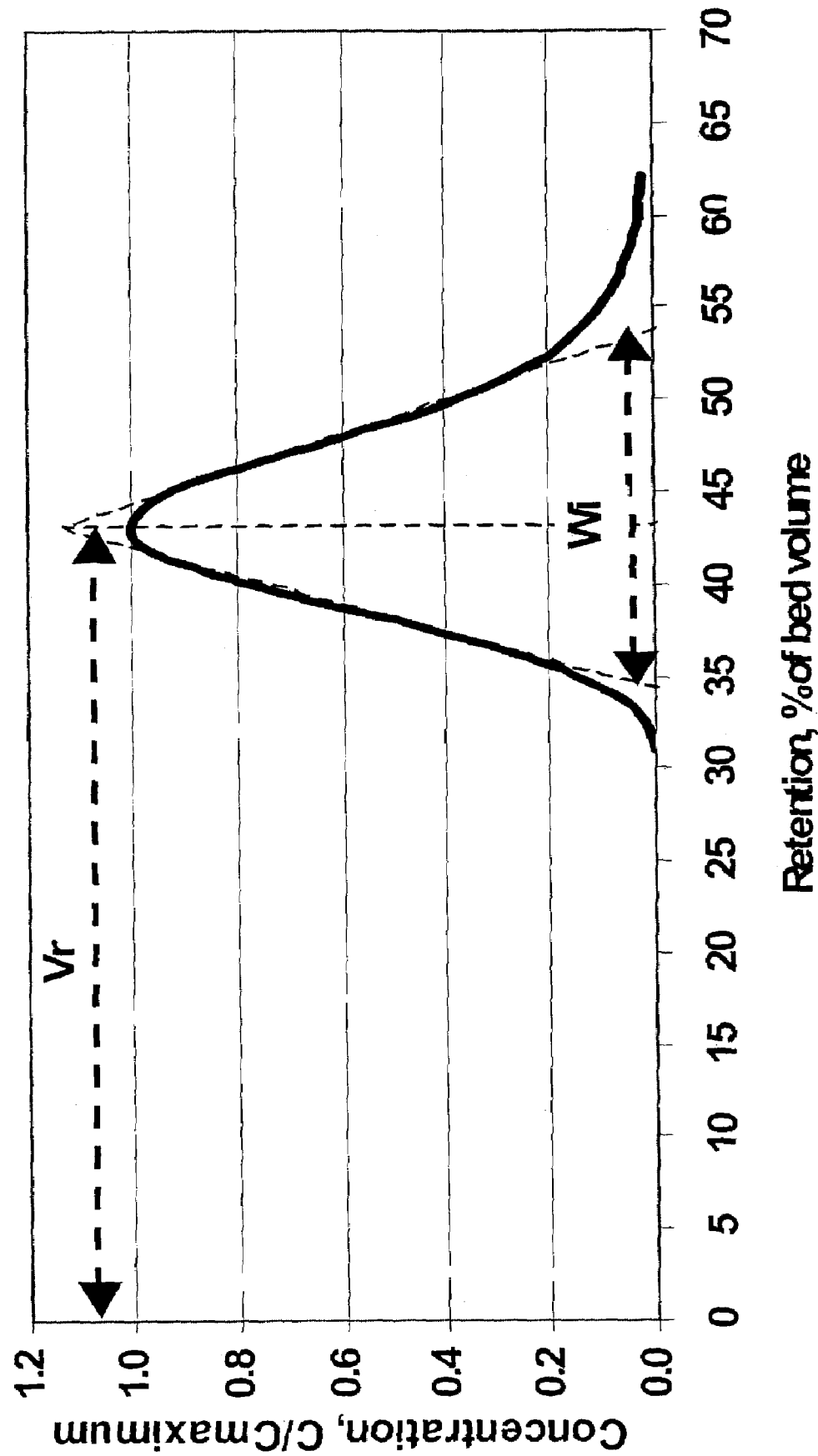
FIG. 12 shows the concentration profile eluted from the test column according to Example 1.

As a feed, 10 weight-% pure sucrose solution was used. The feed and the eluent water were used at a temperature of 85° C. The column and the separation resin were heated with a constant eluent flow. At the first step 40 litres of the feed solution was pumped into the column with a flow rate of 40 l/min. At the second step 500 litres of eluent water was pumped to the column with a flow rate of 40 l/min. In FIG. 12 there is presented concentration profile eluted from the test column.

From the FIG. 12 it can be calculated that the number of theoretical plates (N) is over 70 pcs and height of the theoretical plate (HETP) is less than 1,5 cm. These column efficiency number calculations are based on next equations:

$$N = 16 * (V_r/W_i)^2 \quad (1)$$

$$HETP = L/N \quad (2)$$

Wherein $V_r$ is peak retention as a % of the bed volume $W_i$ is tangential width of the peak as a % of the bed volume L is length of the column In Table 1 there is presented pressure gauge reading values for the pressure gauges P1 and P2 at test conditions with 40 l/min eluent water flow.

TABLE 1

|  | P1 | P2 |
| --- | --- | --- |
| Pressure, bar | 0.91 | 0.79 |

The invention claimed is:

1. A fluid distributing device for distributing fluid into a column comprising:
    a first fluid conveying system (1) for delivering a fluid flow to a plurality of delivering points (2); and
    a distributing plate (3) divided into a plurality of sections (7; 8), wherein each section is served by at least one delivering point (2), wherein each section of the distributing plate comprises
        a fluid transfer port (4) for receiving the fluid flow coming from the delivering point (2) and conveying fluid flow into a plurality of distributing channels (5; 5b) for distributing partial fluid flows into the column, wherein a hydraulic length from the delivering point (2) to points where the partial fluid flows into the column varies; and
        first means (6) for controlling the partial fluid flows by differential pressure, wherein the first means (6) for controlling the partial fluid flows is disposed between the transfer port (4) and the distributing channels (5, 5b).

2. The fluid distributing device according to claim 1, further comprising
    a first connecting channel (5a) disposed between the transfer port (4) and the distributing channels (5b).

3. The fluid distributing device according to claim 2, wherein at least one of the first means (6) for controlling the partial fluid flows is situated upstream to the connecting channel (5a).

4. The fluid distributing device according to claim 2, wherein at least one of the first means (6) for controlling the partial fluid flows is situated downstream to the connecting channel (5a).

5. The fluid distributing device according to claim 2, wherein the first means (6) for controlling the partial fluid flows comprises a nozzle or opening between the fluid transfer port (4) and the connecting channel (5a).

6. The fluid distributing device according to claim 2, wherein the first means (6) for controlling the partial fluid flows comprises a nozzle or opening between the connecting channel (5a) and the distributing channel (5b).

7. The method for distributing fluid into a column characterized in that a fluid distributing device according to claim 2 is used and the method comprises the steps of
    a) feeding the fluid to the first fluid conveying system (1);
    b) delivering the fluid to the delivering points (2);
    c) distributing the fluid from the delivering points (2) into the fluid transfer ports (4);
    d) distributing the fluid from the fluid transfer ports (4) into the distributing channels (5b) through the first means (6) for controlling the partial fluid flows by differential pressure and through the first connecting channels (5a); and
    e) distributing the fluid from the distributing channels (5b) evenly throughout the cross-section of the column.

8. The fluid distributing device according to claim 1, wherein at least one first fluid transfer port (4) is a channel.

9. The fluid distributing device according to claim 1, wherein at least one fluid transfer port (4) is a cavity having a circular or prolate shape.

10. The fluid distributing device according to claim 1, wherein at least one fluid transfer port (4) is connected to the distributing channel (5) through the first means (6) for controlling the partial fluid flows.

11. The fluid distributing device according to claim 1, wherein the first means (6) for controlling the partial fluid flows comprises a nozzle or an opening between the fluid transfer port (4) and the distributing channel (5).

12. The fluid distributing device according to claim 1, wherein the fluid is distributed to the column from at least part of the length of the distributing channels (5; 5b).

13. The fluid distributing device according to claim 12, wherein the cross-sectional area of the distributing channel (5; 5b) diminishes from the first means (6) for controlling the partial fluid flows towards the end of the distributing channel.

* * * * *